United States Patent [19]

Snyder et al.

[11] Patent Number: 5,094,962
[45] Date of Patent: Mar. 10, 1992

[54] MICROPOROUS ARTICLE HAVING A STABILIZED SPECIFIC BINDING REAGENT, A METHOD FOR ITS USE AND A DIAGNOSTIC TEST KIT

[75] Inventors: Brian A. Snyder; Elizabeth A. Grogan; Richard C. Sutton, all of Rochester, N.Y.

[73] Assignee: Eastman Kodak Company, Rochester, N.Y.

[21] Appl. No.: 206,236

[22] Filed: Jun. 13, 1988

[51] Int. Cl.$^5$ .......................................... G01N 33/543
[52] U.S. Cl. .................................... 436/518; 436/524; 436/525; 436/535; 436/808; 436/824; 422/61
[58] Field of Search ............... 436/518, 525, 524, 535, 436/808, 824; 422/61

[56] References Cited

U.S. PATENT DOCUMENTS

| | | | |
|---|---|---|---|
| 3,966,897 | 6/1976 | Renn et al. | 424/1.5 |
| 4,234,316 | 11/1980 | Hevey | 23/230 |
| 4,446,232 | 5/1984 | Liotta | 435/7 |
| 4,632,901 | 12/1986 | Valkirs et al. | 435/5 |
| 4,727,019 | 2/1988 | Valkirs et al. | 435/5 |
| 4,853,335 | 8/1989 | Olsen et al. | 422/60 |
| 4,859,612 | 8/1982 | Cole et al. | 436/525 |

FOREIGN PATENT DOCUMENTS 200381 11/1986 European Pat. Off. .
8703690 6/1987 PCT Int'l Appl. .

Primary Examiner—Robert J. Warden
Assistant Examiner—Lyle A. Alexander
Attorney, Agent, or Firm—J. Lanny Tucker

[57] ABSTRACT

A water-insoluble microporous article comprises a microporous substrate having first and second outer surfaces. Affixed to at least one of those surfaces is a stabilized specific binding reagent admixed with certain hydrophilic, neutral or positively-charged binder materials. Particularly useful binder materials include certain quaternary polymers, vinylpyrrolidone polymers and acrylamide polymers. In this mixture, the reagent exhibits improved keeping stability compared to similar reagents used without binder materials. The reagent comprises water-insoluble particles to which are attached receptor molecules to a target ligand. Substantially none of the reagent is entrapped within the microporous substrate. This article is useful for the detection of a target ligand in an assay involving the specific binding reaction of the ligand with corresponding receptor molecules, and can be included in a diagnostic test kit. It is particularly useful for the detection of Streptococcal antigen in a biological specimen when the receptor molecules are antibodies to that antigen.

23 Claims, No Drawings

MICROPOROUS ARTICLE HAVING A STABILIZED SPECIFIC BINDING REAGENT, A METHOD FOR ITS USE AND A DIAGNOSTIC TEST KIT

FIELD OF THE INVENTION

This invention relates to a microporous article comprising a stabilized specific binding reagent, and to its use in a method for detecting a target ligand. It also relates to a diagnostic test kit comprising the article. The invention is useful in diagnostic methods.

BACKGROUND OF THE INVENTION

There is a continuing need in medical practice, reserch and diagnostic procedures for rapid and accurate detection or quantification of biological and chemical substances which are present in biological fluids, cells or tissues. For example, the presence of drugs, hormones, steroids, polypeptides, nucleotides, prostaglandins, proteins, carbohydrates or infectious organisms (bacteria, fungi or viruses) in biological specimens has to be determined in an accurate and rapid fashion for suitable diagnosis or treatment.

For example, organisms classified as gram positive bacteria, such as group specific Streptococcus, are known to be pathogenic in humans. For instance, Group A organisms are primarily responsible for causing B-hemolytic pneumonia, scarlet fever, rheumatic fever, cardiac sequelae, glomerulonephritis, septic sore throat and puerpueral sepsis. Because of the serious nature of infections potentially caused by Streptococcus A, it is important to diagnose its presence at an early stage so that an appropriate course of treatment can be pursued. In most cases, the diagnostic tests require several hours, or at least up to 30 minutes. Even this limited wait may be intolerable in many instances where the practitioner has many waiting patients, and the patients themselves can not wait for the diagnosis without considerable cost, inconvenience or discomfort.

To provide diagnostic determinations, various methods have been devised for isolating and identifying biological or chemical substances employing specific binding reactions between the substance to be detected (identified as a "target ligand" or simply "ligand" herein) and receptors (compound which specifically react or bind with that substance). This reaction between a ligand and its corresponding receptor is known as a specific binding reaction. Where either the ligand or receptor is an antibody, the reaction is known as an immunological reaction. More than one ligand or receptor may participate in each reaction.

Such reactions are detected in a number of ways. Generally, one or more participants of the specific binding reaction is detectably labeled. That is, it is either chosen because it is inherently detectable, or a detectable moiety (for example, an enzyme, radioisotope, chromogen or fluorogen) is incorporated therein in some manner.

Furthermore, it is often necessary in detecting the products of the specific binding reactions described above that the products be insolubilized in some manner and separated from unreacted materials. Various insolubilizing means have been used including particles, the sides of containers such as test tubes, thin films and others known in the art. In some assays and diagnostic devices, a receptor for the ligand is bound to a porous membrane or filter, such as described in related U.S. Pat. Nos. 4,632,901 (issued Dec. 30, 1986 to Valkirs et al) and 4,727,019 (issued Feb. 23, 1988 to Valkirs et al). These membranes or filters serve both to insolubilize the resulting complex as well as to separate it from uncomplexed materials by filtration.

PCT Publication 87/03690 (published June 18, 1987) also describes the use of a porous filtration membrane in an immunoassay wherein an insolubilized immunocomplex is trapped in the membrane as fluid drains through. The insolubilized immunoreagents can be incorporated into the membrane prior to the assay for storage. A similar solid phase membrane system is described in E. P. Publication 200,381 (published Nov. 5, 1986). Microspheres having receptor molecules attached thereto are entrapped within a porous matrix. A similar diagnostic test for Streptococcus A antigen has been commercially available for about two years.

However, assays carried out using entrapped reagents lack sufficient sensitivity and detectability of the complex in order to provide highly successful assays in the marketplace.

A diagnostic test kit for Streptococcus A determination, which has been marketed by Hybritech, Inc. for about two years as the Tandem ® Icon ® Strep A test, has particulate immunoreagents coated on top of a membrane. However, this test kit has disadvantages, namely low sensitivity for samples with low colony counts and slow assay dye kinetics.

Moreover, it has been found that specific binding reagent affixed to the microporous substrate lacks sufficient keeping stability for the lengthy times often required for manufacture, shipping and storage prior to use. If the reagent is used relatively soon after manufacture, stability is not a serious problem. However, a diagnostic test device shipped a considerable distance from the site of manufacture (for example, remote or underdeveloped areas of the world) must have acceptable refrigerator and room temperature keeping stability over several weeks or months to assure accurate and sensitive results when it is eventually used. Such a product useful for various diagnostic assays, and particularly to detect Streptococcal antigens, would be greatly welcome in the industry.

SUMMARY OF THE INVENTION

Significantly improved keeping stability is achieved with a water-insoluble microporous article for use in a ligand-receptor assay to detect a target ligand, the article comprising a microporous substrate having at least first and second opposing outer surfaces, and having affixed to at least one of the surfaces a composition comprising a specific binding reagent which comprises water-insoluble particles to which are attached receptor molecules to the target ligand, the reagent admixed with one or more hydrophilic, neutral or positively-charged polymeric binders.

A method for the detection of a target ligand in a biological specimen comprises the steps of:

A. contacting a sample of a biological specimen suspected of containing a target ligand with the water-insoluble microporous article described above, to form a specific binding complex between the target ligand and the receptor molecules, and B. detecting the presence of the complex as an indication of the presence of the ligand in the specimen.

Further, a diagnostic test kit useful for the detection of a target ligand comprises:

a. the water-insoluble microporous article described above, and b. detectably labeled receptor molecules.

The present invention provides a rapid and accurate method for detecting a variety of ligands in biological specimens. In particular, the method is useful for detecting a Streptococcal antigen, such as the Streptococcal A antigen. The method can generally provide a definitive result in just a few minutes, such as less than about 10 minutes including antigen extraction is needed. Moreover, the assay is highly sensitive to low levels of ligand because the resulting detectable complex is on the outer surface of the microporous substrate. A significant advantage is the improved keeping stability for the reagent on the microporous article.

These advantages are achieved by using a microporous article having the particulate specific binding reagent affixed to the outer surface thereof, and which reagent is admixed with a hydrophilic neutral or positively-charged binder material. The comparative results provided below illustrate the unexpected improvement achieved with this invention.

DETAILED DESCRIPTION OF THE INVENTION

The present invention can be used to rapidly detect the presence of a target ligand in a biological specimen from human or animal hosts. As noted above, this ligand can be any chemical or biological substance for which there is corresponding receptor which specifically reacts therewith to form a complex. Representative ligands include, but are not limited to, proteins (such as enzymes, antibodies and antigenic proteins and fragments thereof), peptides, polypeptides, nucleotides, carbohydrates, plant lectins, toxins, haptens, drugs, viruses, fungi and bacteria and components thereof, and other materials known to one skilled in the art. This invention is particularly useful for the detection of Streptococcal antigens, such as the carbohydrate antigens extracted from Streptococcal A, B, C or G group organisms. Streptococcal A antigen is most particularly detectable with this invention.

Biological samples which can be so assayed include, but are not limited to, whole blood or a component (serum or plasma) thereof, saliva or mucous from the throat or mouth, lacrimal fluid, spinal fluid, feces, urine, vaginal secretions, seminal fluid, human tissue or organ extracts and human milk. The specimens can be collected using suitable procedures. For example, a throat swab specimen is generally assayed in the detection of Streptococcal antigens.

A critical aspect of the present invention is the use of the water-insoluble microporous article described above. This article is composed of a microporous substrate which has first and second outer surfaces. The substrate is inert to any chemical or biological reactions and is generally composed of one or more natural or synthetic substances which have sufficient integrity for affixing the reagent described below, and porosity for suitable filtration in the assay. Useful materials include, but are not limited to, natural or synthetic polymers, sintered glass, membranes or filters of glass or polymeric films or fibers, ceramic materials, cellulosic materials, particulate structures composed of beads bound together with an adhesive or binder material. One skilled in the art can readily determine many commerically available materials or design others which are useful in this invention. Particularly useful materials are the polyamide (particularly, nylon) microporous membranes commercially available from Pall Corp.

The microporous substrate has at least two outer surfaces which oppose each other. Generally, these opposing surfaces are the upper and lower surfaces of a microporous membrane. This is to distinguish the article from multilayer analytical elements known in the art which have one or more porous adjacent layers. Such elements generally have all reagents within the layers, and none affixed to an outer surface.

The article is designed such that it has sufficient porosity to quickly drain away fluid and uncomplexed materials encountered during an assay. Such uncomplexed materials include uncomplexed ligand, receptor molecules, cellular debris and other nonparticulate extraneous matter from a biological specimen. Therefore, the pore size of the microporous substrate must be such that the noted materials will pass through the porous substrate. Moreover, while some of the reagents may become entrapped within the pores of the article, the pore size generally will not accommodate a significant portion of the particulate reagent used in the assay. It is highly preferred that substantially all of the reagent is on the article's outer surface. While it is not required, the reagent is somewhat aggregated or bound together by chemical or mechanical means, so it does not readily enter the porous substrate. Generally, this requires the average pore size to be less than about five times the average size (for example, the diameter of spherical particles) of the reagent. For preferred membranes, the average pore size is from about 0.5 to about 10 $\mu$m.

If desired, the microporous substrate can be coated with proteins (such as casein or succinylated casein, as described in copending and commonly assigned U.S. Ser. No. 098,433, filed Sept. 18, 1987 by Snyder et al) to reduce nonspecific interactions, or by surfactants to promote rapid filtration, or other optional materials which may facilitate the assay.

The specific binding reagent (described in more detail below) is located on one or more of the outer opposing surfaces. It can be affixed to the surface in any suitable manner as long as the receptor in the reagent is available for reaction with ligand in the contacting specimen. Generally, the reagent is affixed such that moderate mechanical disturbance during manufacture and handling does not loosen the reagent. Moreover, the reagent generally does not come off the substrate during an assay. For example, the reagent can be affixed mechanically by coating, spotting or spraying and held thereon by hydrophobic bonding among reagent particles as well as between particles and substrate. It can also be covalently affixed by suitable chemical reaction.

In the present invention, it is critical for keeping stability of the reagent that it be admixed with a hydrophilic, neutral or positively-charged binder material, thereby forming a specific binding composition. It should be noted, however, that this type of binder material is not necessarily contributing to the affixation of the reagent to the substrate, or to the binding among the particles. Rather, the binder material improves the keeping stability of the reagent considerably over the same reagent used without the binder material. Generally, the hydrophilic binder is present in an amount which will not significantly adversely affect either the specific binding capacity of the reagent or the porosity of the microporous article. The amount of binder material is generally less than 20% based on the total weight of reagent, and preferably the amount is from about 1 to about 10%. A most preferred amount is from about 2.5 to about 7.5%.

In general, useful hydrophilic, neutral or positively-charged binders include polymers which maintain at least about 80% original reagent stability after reagent keeping for at least about 2 months at 20°–25° C. and 30–50% relative humidity. Particularly useful binders include, but are not limited to, vinylpyrrolidone polymers, acrylamide polymers, and polymers containing quaternary salts and other known in the art which are either neutral in charge or positively charged. By "neutral in charge" is meant that either the polymer has no charges, or has both negative and positive charges which provide a net zero charge in the molecule. The polymers can be homo- or copolymers, and used singly or in combination. Acrylamide polymers are also defined to include methacrylamide polymers. Representative polymers include (with weight ratios of monomers): poly(acrylamide), poly(methacrylamide), poly(acrylamide-co-N-vinyl-2-pyrrolidone)(90:10), poly(N-vinyl-2-pyrrolidone), poly(acrylamide-co-N-vinyl-2-pyrrolidone)(50:50), poly(methacrylamide-co-4-vinyl-N-methylpyridinium methosulfate)(75:25), poly(acrylamide-co-N-vinylimidazole)(90:10), poly(acrylamide-co-N-vinyl-3-methylimidazolium methosulfate)(90:10), poly[2-(N,N,N-trimethylammonium)ethyl methacrylate chloride-co-2-hydroxyethyl acrylate](90:10), poly[2-(N,N,N-triethylammonium)ethyl acrylate methosulfate-co-N-vinyl-2-pyrrolidone](50:50), poly(1,2-dimethyl-5-vinylpyridinium methosulfate-co-acrylamide)(50:50), poly(3-methyl-N-vinylimidazolium methosulfate-co-N-vinyl-2-pyrrolidone)(60:40), poly(N-vinyl-3-methylimidazolium methosulfate-co-N-vinyl-2-pyrrolidone)(75:25), poly[2-(N,N,N-trimethylammonium)ethyl methacrylate fluoride], poly(-dimethyldiallylammonium chloride) and poly[2-(N,N,N-trimethylammonium)ethylmethacrylate chloride-co-acrylamide](50:50).

Other useful positively-charged polymeric binders include mordants described in U.S. Pat. No. 4,069,017 (issued Jan. 17, 1978 to Wu et al) and references mentioned therein, with the proviso that the mordants are sufficiently water-soluble. Sufficient water-solubility is generally provided by having at least 50% by weight of the polymer be composed of monomers containing the positively-charged groups.

Particularly useful binders are polymers containing quaternary ammonium salts, vinylpyrrolidone polymers and acrylamide polymers.

Most preferably, the reagent used in the practice of this invention is substantially on the surface of the substrate, meaning that less than 5% (by weight of reagent) is entrapped within the microporous substrate. Preferably, less than 1% (by weight) is so entrapped. By "entrapped" is meant that the entire reagent particle is within a pore of the substrate. This does not mean that reagent particles cannot be partially embedded in pores at or near the outer surface of the substrate. Unintentionally, the microporous substrate may have some reagent partially embedded in its pores, but, as defined above, substantially none of it will be entrapped therein, as opposed to the porous articles described in PCT Publication 87/03690 and E. P. Publication 200,381 (both noted above).

The reagent can be affixed to a substrate surface in one or more discrete zones of the surface, each zone representing less than the total surface area. Alternatively, the reagent can be affixed to the entire surface area. In a preferred embodiment, the reagent is affixed in a central zone of the surface. Different binder materials can be used in individual zones for reagent keeping stability.

The specific binding reagent used in this invention comprises a water-insoluble particle which is inert to all chemical and biological reactions other than reactions needed to attach receptor molecules. The particles are preferably spherical in shape, but the structural and spatial configurations are not critical. For instance, the particles can be cubic, ellipsoidal or fibrous in shape. Generally, the largest dimension of the particles is on the average of about 3 μm. Preferably, the spherical particles used are from about 0.01 to about 5 μm in diameter.

The particles can be prepared from any natural or synthetic water-insoluble material. Alternatively, they can be solid particulate organisms, such as *Staphylococcus aureus* or *Toxoplasma gondii*. Preferably, however, the particles are prepared from glass, ceramics, magnetic materials, natural or synthetic polymers, diatomaceous earth, proteins and other nonliving particulate materials known in the art.

Whatever the material used for the particles, it must be suitable for attaching receptor molecules to the outer surface thereof. In some instances, the receptor molecules are readily adsorbed onto the particles whereas other particles may require modest pretreatment for suitable attachment. The receptors may also be modified in a manner suitable for adsorption or covalent attachment. A skilled worker in the art would readily understand how to match particles with receptors using any needed reactions, pretreatments or linking materials. Some reagents are commercially available.

Preferred reagents are prepared using polymeric particles which have suitable reactive groups for covalently attaching the receptor molecules thereto. The density of the receptor molecules may vary depending upon the composition of the particles, their size and the type of receptor, but sufficient density is needed for adequate sensitivity in the assay. Covalent attachment of receptor is usually accomplished using surface reactive groups which are capable of reacting directly or indirectly (that is through linkages, such as proteins or avidin-biotin) with free amine or sulfhydryl groups of the ligand. Such surface reactive groups include, but are not limited to, carboxy, epoxy, aldehyde, active halo atoms, activated 2-substituted ethylsulfonyl, vinylsulfonyl and other groups known in the art. The following discussion regarding preferred embodiments is for exemplification only, and is not meant to be limiting.

Particularly useful polymeric particles include those described in copending and commonly assigned U.S. Ser. No. 081,206, filed Aug. 3, 1987 by Sutton et al. Such particles are generally water-insoluble latex particles having an average particle size greater than about 0.01 micrometers. They are composed of polymers prepared from one or more ethylenically unsaturated polymerizable monomers at least one of which has active halo atoms or activated 2-substituted ethylsulfonyl or vinylsulfonyl groups.

Monomers having an active halogen atom include vinyl chloroacetate, vinyl bromoacetate, 4-(3-chloropropionamido)styrene, N-(3-chloropropionamidocarbonyl)acrylamide, 4-(chloroacetamido)styrene, haloalkylated vinyl aromatics (for example, chloromethylstyrene or bromomethylstyrene), haloalkyl acrylic or methacrylic esters (for example, chloroethyl methacrylate, 3-chloro-2-hydroxypropyl methacrylate and 3-chloropropyl acrylate) and others known to one skilled in the art. The haloalkylated vinyl aromatics, for example those having active haloalkyl groups of 1 to 3 carbon atoms, are preferred when the active halogen atom is used as the reactive group. Chloromethylstyrene is most preferred.

Preferred activated 2-substituted ethylsulfonyl and vinylsulfonyl monomers can be represented by the formula (I):

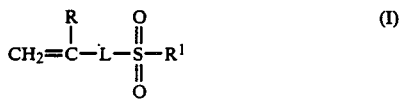

wherein R is hydrogen or substituted or unsubstituted alkyl (generally of 1 to 6 carbon atoms, such as methyl, ethyl, isopropyl or hexyl). Preferably, R is hydrogen or methyl.

$R^1$ is —CH=CHR$^2$ or —CH$_2$CH$_2$X wherein X is a leaving group which is displaced by a necleophile or is eliminated in the form of HX by treatment with a base (such as halo, acetoxy, alkylsulfonyloxy such as methylsulfonyloxy, arylsulfonyloxy such as p-tolylsulfonyloxy, trialkylammonio, for example, a trimethylammonio salt or pyridinio salt). $R^2$ is hydrogen, substituted or unsubstituted alkyl (generally of 1 to 6 carbon atoms as defined for R), or substituted or unsubstituted aryl (generally of 6 to 12 nuclear carbon atoms, such as phenyl, naphthyl, xylyl or tolyl). Preferably, $R^1$ is —CH$_2$CH$_2$X. This group, which is an activated 2-substituted ethyl group, can be substituted with any group which does not impair the displacement of the leaving group X.

L is a linking group which can be a substituted or unsubstituted alkylene generally having 1 to 20 carbon and hetero atoms in the backbone. This definition of alkylene is meant to include alkylene groups interrupted or terminated with oxy, thio, —NR$^3$— [wherein R$^3$ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl or xylyl)], ester (—COO—), amide (—CONH—), urylene

sulfonyl (—SO$_2$—), carbonate, sulfonamide, azo, phosphono or other similar groups. Representative alkylene groups include methylene, ethylene, isobutylene, hexamethylene, carbonyloxyethyleneoxycarbonylethylene, methylenebis(iminocarbonyl)ethylene, carbonyloxydodecylenecarbonyloxyethylene, carbonyliminomethyleneiminocarbonyliminoethylene, carbonyliminomethyleneiminocarbonylethylene and other groups described or suggested by U.S. Pat. Nos. 4,161,407 and 4,548,870.

L can also be substituted or unsubstituted arylene generally having 6 to 12 nuclear carbon atoms. Representative arylene groups include phenylene, tolylene, naphthylene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art), as well as such combinations which are interrupted or terminated by one or more amide or ester groups (for example, carbonyliminoarylenealkylene). Preferably, L is substituted or unsubstituted phenylenealkylene [for example, substituted with one or more alkyl groups (as defined for R), alkoxy groups (generally of 1 to 6 carbon atoms, for example, methoxy, propoxy or butoxy) or halo groups], carbonyliminoarylenealkylene (wherein arylene and alkylene are defined above), or carbonyliminoalkyleneiminocarbonylalkylene (wherein alkylene are defined above).

Representative useful monomers include m and p-(2-chloroethylsulfonylmethyl)styrene, m and p-[2-(p-tolylsulfonyloxy)ethylsulfonylmethyl]styrene, m and p-vinylsulfonylmethylstyrene, N-[m and p-(2-chloroethylsulfonylmethyl)phenyl]acrylamide, and N-[2-(2-chloroethylsulfonyl)ethylformamidomethyl]acrylamide. The first monomer is preferred.

One or more of the monomers described above can be polymerized individually or in combination to form homo- or copolymers. Alternatively, and preferably, one or more of them are copolymerized with at least one other ethylenically unsaturated polymerizable monomer. Generally such monomers provide various desirable properties such as hydrophobicity, dispersibility or other features. Particularly useful comonomers are described in copending U.S. Ser. No. 081,206 (noted above).

Representative useful polymers include the following: poly(m and p-chloromethylstyrene), poly(styrene-co-m and p-chloromethylstyrene-co-2-hydroxyethyl acrylate) (67:30:3 molar ratio), poly(styrene-co-m and p-chloroethylsulfonylmethylstyrene) (95.5:4.5 molar ratio), poly{styrene-co-N-[m and p-(2-chloroethylsulfonylmethyl)phenyl]-acrylamide} (99.3:0.7 molar ratio), poly(m and p-chloromethylstyrene-co-methacrylic acid) (95:5, 98:2 and 99.8:0.2 molar ratio), poly(styrene-co-m and p-chloroethylsulfonylmethylstyrene-co-methacrylic acid) (93.5:4.5:2 molar ratio), poly{styrene-co-N-[m and p-(2-chloroethylsulfonylmethyl)phenyl]acryl-amide-co-methacrylic acid} (97.3:0.7:2 molar ratio), and poly(styrene-co-m and p-chloromethylstyrene) (70:30 molar ratio).

In preparing a specific binding reagent, receptor (for example, antibodies to Streptococcal antigen) is generally mixed with the particles under suitable conditions depending upon the method of attachment (absorption, covalent or use of linking groups). A worker skilled in the art would readily determine the appropriate conditions from the considerable teaching in the art, as well as the exemplary procedures taught herein. For example, for attachment to the preferred particles described above having reactive halo atoms, activated 2-substituted ethylsulfonyl or vinylsulfonyl groups, the receptor is generally mixed with the particles for up to 24 hours at a temperature of from about 20° to about 40° C. The particle suspension is generally buffered to a pH of from about 7 to about 10. In the mixture, particles are generally present in an amount of at least about 0.2 weight percent, and receptor is generally present in an amount of at least about 1% (based on total weight of particles).

The receptor molecules used in preparing the reagent can be obtained commercially or by using known extraction, culturing or immunological procedures. For example, if the receptor is an antigenic material used to detect an antibody, the antigenic material can be either extracted from an organism or infected host using known techniques. If the receptor is an antibody, they often are available commercially. If not, they can be prepared using standard immunochemical techniques including hybridoma technology for producing monoclonal antibodies. Either whole or fragments of biological or chemical substances can be used as receptor molecules.

The reagent used in this invention can be detectably labeled. By "detachably labeled" is meant that the reagent has associated with it (either as part of the particles or receptor molecule) a moiety which can be detected using suitable procedures and equipment or reactive compositions. Such labels include enzymes, radioisotopes, chemiluminescent moieties, chromogens, fluorogens, phosphorescent moieties, biotin or similar detectable compounds, enzyme inhibitors or activators, and others known to one skilled in the art. "By associated with" is meant that the label is attached to, incorporated therein or otherwise proximate to the reagent so that the reagent's presence is directly or indirectly detectable by proportional presence of the label. Preferably, the reagent is unlabeled and is used in assays described below wherein a separate labeled receptor or ligand is involved.

The specific binding composition comprising the reagent described above can be applied to the porous substrate in any suitable manner which affixes it to the outer surface as noted above. Coating, deposition or merely dropping it onto the surface in appropriate solvents (such as water, a buffer or organic solvent which will not harm the receptor) under suitable conditions is acceptable. Generally, the composition is dried before use in an assay although that is not necessary.

The water-insoluble article of this invention can be used in an assay without other equipment or test containers, if so desired (for example, as a hand-held article through which fluid is drained into container). Generally, however, it is mounted as part of a test device. Various test devices are known in the art including those described in U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May 1, 1984 to Liotta). Particularly useful devices are described in U.S. Ser. No. 098,248 (filed Sept. 18, 1987 by Hinckley et al) now abandoned and in U.S. Ser. No. 136,211 (filed Dec. 18, 1987 by Smith-Lewis), now U.S. Pat. No. 4,870,007.

More specifically, the test device comprises a water-insoluble shell having one or more test wells therein, each of which can accommodate a sample of a biological specimen and appropriate reagents.

The shell can be prepared from any useful water-insoluble material such as glass, polymeric materials, ceramics, fibrous materials, cellulosic materials and other materials known in the art.

In a preferred embodiment, the test device has three test wells designed for providing a specimen test result and positive and negative control results. Each test well has a microporous article mounted therein, and at least one of the test wells has the microporous article of the present invention mounted therein. Another test device is described in U.S. Ser. No. 019,810 (filed Feb. 27, 1987 by Hinckley), now U.S. Pat. No. 4,833,087 and U.S. Ser. No. 098,248 (filed Sept. 18, 1987 by Hinckley et al), now abandoned. Other variations of useful test devices would be within the purview of a worker of ordinary skill in the art.

Having described the article of this invention in general, a preferred embodiment of the invention is a water-insoluble microporous article for use in an immunoassay to detect Streptococcus A, the article comprising a microporous membrane having upper and lower outer surfaces and an average pore size of from about 0.5 to about 10 $\mu$m, and having affixed to the upper surface a composition comprising an unlabeled specific binding reagent which comprises water-insoluble polymeric particles having an average diameter of from about 0.1 to about 10 $\mu$m and to which are attached antibodies to Streptococcal A antigen, said reagent being admixed with one or more hydrophilic homo- or copolymer binders derived from monomers containing quaternary salts, vinylpyrrolidone monomers or acrylamide monomers.

Generally, the method of this invention is carried out by contacting the article of this invention with a sample of a biological specimen suspected of containing a target ligand in such a manner as to form a specific binding complex between the target ligand and the receptor molecules in the reagent. This contact can be accomplished in any suitable manner, but preferably the specimen is applied to the article which is generally in a test device.

The complex thereby formed is then detected in a suitable manner as an indication of the presence of the ligand in the specimen. Detection will depend upon the type of assay being carried out and the type of label used if any, and appropriate reaction compositions, equipment and detection procedures are well known. If the reagent is appropriately labeled, detection may be done visually or with suitable spectrophotometric or radiometric equipment.

The assay can also be what is known as a competitive binding immunoassay in which a measured amount of labeled ligand is allowed to react with the reagent receptor as well as ligand in the specimen. Moreover, it is possible to indirectly measure ligand by contacting it with both labeled and unlabeled reagent affixed to the article of this invention. The specific details of such assays are well within the purview of one of ordinary skill in the art.

In a preferred embodiment, the method involves the complexation of ligand with the reagent as well as the complexation of the ligand with one or more of the same or different receptors, one of which is insolubilized, and one of which is detectably labeled. The complexation with the same or different receptors can occur prior to, simultaneously with or subsequent to complexation with the reagent on the article.

For instance, the ligand can be complexed with a water-soluble, detectably labeled (as described above) second receptor as well as with the reagent. This is generally known in the art as an immunometric or "sandwich" assay. The labels can be as described above, but are preferably radioisotopes or enzymes, and more preferably, enzymes (such as peroxidase, alkaline phosphatase, glucose oxidase, urease or $\beta$-galactosidase). The receptors can be the same or different as long as they do not inhibit the complexation of ligand with the other.

Alternatively, the ligand can be complexed with a second unlabeled receptor which is then complexed with a third receptor which is detectably labeled. Any number of receptors can be used in such situations as are necessary for attaching labels or other useful moieties.

The following preferred embodiment relating to an assay for a Streptococcal antigen is meant to be exemplary, not limiting.

A method for the detection of a Streptococcal antigen in a biological specimen comprises the steps of:

A. contacting a sample of a biological specimen suspected of containing extracted Streptococcal antigen with a water-insoluble microporous article, the article comprising a microporous membrane having upper and lower outer surfaces, and having affixed to the upper surface a composition comprising an unlabeled specific binding reagent which comprises water-insoluble polymeric particles to which are attached antibodies to the Streptococcal antigen, said reagent being admixed with one or more hydrophilic homo- or copolymer binders as described herein to form a specific binding complex between the Streptococcal antigen and the antibodies, B. prior to, simultaneously with or subsequent to the contact in step A, contacting the Streptococcal antigen with a detectably labeled antibody to the antigen so as to form a labeled specific binding complex of the antigen with both the labeled reagent and unlabeled antibodies, C. simultaneously with or subsequent to contacting step B, separating the labeled complex from uncomplexed materials by washing uncomplexed materials through the membrane, and D. detecting the labeled complex as an indication of the presence of the Streptococcal antigen in the specimen.

Extracted Streptococcal antigen can be obtained from a biological specimen (for example, a throat swab specimen) using any suitable extraction technique including hot formamide, autoclaving in the presence of HCl, use of various enzymes (such as Streptomyces albus, U.S. Pat. No. 4,618,576, issued Oct. 21, 1986 to Rosenstein et al), or by the generation of nitrous acid according to U.S. Pat. No. 4,673,639 (issued June 16, 1987 to Slifkin). A preferred extraction technique uniquely different from the Slifkin approach is described in U.S. Ser. No. 131,618 (filed Dec. 11, 1987 by Snyder et al), now U.S. Pat. No. 4,808,524 which is incorporated herein by reference.

The extracted antigen is then contacted with the microporous article as described above to form the antigen-antibody complex. A brief incubation period may be desirable to enhance complex formation, but usually it is less than 5, and preferably less than 2, minutes at room temperature.

A labeled complex is formed using a detectably labeled antibody to the Streptococcal antigen. The labeled antibody can be reacted with the antigen prior to, simultaneously with or subsequent to contact with the reagent on the membrane. Preferably, it is reacted subsequent to that contact.

Separation of the resulting complex from uncomplexed materials occurs virtually simultaneously with complex formation. However, if desired, the reactants and fluid can be held on the membrane for a brief period of time to insure complete reaction. Separation then takes but a few seconds once fluid is allowed to drain. The insoluble labeled complex of antigen and two or more antibodies is retained on the membrane. One or more washes may be applied if desired to enhance separation. A preferred wash solution is described and claimed in copending and commonly assigned U.S. Ser. No. 155,441, filed Feb. 12, 1988 by Warren III et al.

The labeled complex is then suitably detected. Preferably, the label is an enzyme, and a suitable dye-forming composition is added to provide a dye (chromogen or fluorogen) in the presence of the enzyme and its substrate. Peroxidase is a preferred enzyme label, and a number of suitable dye-forming compositions are known comprising a substrate or substrate-forming reactants as well as dye-forming reactants. The substrate itself can be a dye-forming compound, such as benzidine, tetramethylbenzidine or other benzidine derivatives, 2,2'-azino-di-(3-ethyl-benzthiazolone-6-sulfonic acid), phenol red, o-phenylenediamine, pyrogallol, 4-aminoantipyrine, bromopyrogallol red and others known in the art. Alternatively, a hydrogen donor and an electron acceptor can be combined to provide a detectable species (for example, see the compounds described in U.S. Pat. No. 4,260,679).

Preferably, the dye-forming composition includes a leuco dye which provides a dye in the presence of hydrogen peroxide and peroxidase [for example, a triarylimidazole leuco dye as described in U.S. Pat. Nos. 4,089,747 (issued May 16, 1978 to Brushci) or a triarylmethane leuco dye as described in 4,670,385 (issued June 2, 1987 to Babb et al)]. A preferred dye-providing composition is described and claimed in copending and commonly assigned U.S. Ser. No. 136,166, filed Dec. 18, 1987 by McClune.

Once a dye has been formed in the presence of the insoluble complex, it can be evaluated visually or by using spectrophotometric equipment to determine if the assay indicates the presence of antigen in the specimen. Both positive and negative control tests may be desirably carried out with the specimen test. Appropriate reagents could be used for each control test to give the desired result.

The diagnostic test kit of this invention includes the article of this invention as well as detectably labeled receptor molecules for the target ligand. These kit components can be packaged in a suitable manner and included in a carrier of some type which can be compartmentalized to receive the article (alone or in a test device) and vials or bottles of liquid or solid reagents. In addition, it can also include one or more of the following which are useful in carrying out the method: dye-forming composition, extraction reagents (if the ligand must be extracted before the assay), wash solutions, diluents, further receptor molecules and other reagents known to one skilled in the art for a given assay. Reagents can be provided in dry form or in appropriate solutions. Non-reactive components of the kit can include instructions, mixing vessels, stirring means, pipettes and the like.

The following examples are representative of the practice of this invention but are not intended to limit it. All percentages are by weight unless otherwise indicated.

MATERIALS

Anti-Streptococcus A-peroxidase conjugate was prepared using immunopurified rabbit polyclonal antibodies which were obtained commercially and horseradish peroxidase from Miles Laboratories (Elkhart, Ind.) by the method described by Yoshitake et al, *Eur. J. Biochem.* 101, 395 (1979). The conjugates were used in a composition comprising succinylated casein in buffer as described in copending and commonly assigned U.S. Ser. No. 206,257, filed on even date herewith by Warren and Snyder and entitled "Specific Binding Composition Comprising a Low pI Protein or Carbohydrate and a Diagnostic Test Kit and Method of Use".

A leuco dye solution was prepared with 2-(4-hydroxy-3,5-dimethoxyphenyl)-4,5-bis(4-methoxyphenyl)imidazole as follows:

Solid leuco dye (to make a 0.1% solution) was dissolved in a solution of 20% poly(vinylpyrrolidone) in sodium phosphate buffer (5 mmolar). This solution was then added to a solution containing hydrogen peroxide (10 mmolar), 4'-hydroxyacetanilide electron transfer agent (0.7 mmolar) and diethylenetriaminepentaacetic acid chelating agent (10 µmolar) in sodium phosphate buffer to produce a final concentration of 1% poly(vinylpyrrolidone) and 0.005% leuco dye. This composition is described and claimed in copending and commonly assigned U.S. Ser. No. 206,257 filed on even date herewith by Snyder, Warren III and McClune and entitled "Imidazole Leuco Dye Composition Containing 4'-Hydroxyacetanilide, Diagnostic Kit and Method Using Same".

Succinylated casein was prepared by reacting casein with an equal weight of succinic anhydride for four hours at 25° C., then purifying the product by dialysis.

The buffers mentioned and used herein are available from a number of commercial sources including Sigma Chemical Co. (St. Louis, Mo.).

LoProdyne TM nylon microporous membranes were obtained from Pall Corp., incorporated into the test wells of a disposable test device and pretreated with Fluorad FC 135 surfactant (0.05 g/m², available from 3M Co.).

EXAMPLE 1

Assay for Streptococcus A Antigen

This example demonstrates the use of the microporous article of this invention in the method of this invention to detect Streptococcus A antigen in a biological specimen, and a comparison of binding reagent stability.

The following specific binding reagents were evaluated:

Invention: The reagent was mixed with poly(acrylamide) binder (5%).

Control A: The reagent was used without a binder.

Control B: The reagent was mixed with poly(acrylamide) (5%) in combination with bovine serum albumin (0.1%, a negatively-charged protein).

Control C: The reagent was mixed only with bovine serum albumin (0.1%).

Streptococcus A antigen was obtained from Group A strep cultures using a standard nitrous acid extraction wherein aqueous sodium nitrite was mixed with an acidic coreagent prior to the addition of the cultured organism. The extraction fluid was then neutralized by the addition of excess buffer. The Group A carbohydrate antigen was obtained using acidic ethanol and acetone, discarding the supernatant and resuspending the pellet in 0.85% saline solution. The concentration of rhamnose was determined by the method of Dische and Shattles, J. Biol. Chem. 175, 595–603 (1948). This concentration was resuspended in the neutralized extraction medium comprising citric acid (10 µl, 1.2 molar), sodium nitrite solution (120 µl, 8 molar) and 4-morpholinopropane sulfonic acid buffer (120 µl, 2 molar, pH 8).

A microporous membrane as described above was incorporated into the test wells of disposable test devices which were similar to that described in U.S. Ser. No. 098,248 (noted above). In these examples, all wells in the test devices were used as test wells, that is the tests were run in triplicate. A dispersion of the specific binding reagent comprising poly[styrene-co-m and p-(2-chloroethylsulfonylmethyl)-styrene] beads [2 µl of a 1% solid suspension (in 0.1 molar glycine buffer, pH 8.5), admixed with binding reagents described above and 0.0005%, of an optical brightener], was added to the center area of the membrane in the wells.

Some of the disposable test devices were tested for performance with a given level of Streptococcus A antigen. Others were then put into heat sealed containers and kept at 37° C. and 30–50% relative humidity for four weeks accelerated keeping tests, followed by use in the assay described below.

Antigen sample (200 µl containing about 20 ng/ml of carbohydrate) was added to various disposables containing the different specific binding reagents, and drained. The conjugate solution (40 µl) containing conjugate (9 µg/ml) and succinylated casein (0.5%,) in 4-morpholinopropane sulfonic acid buffer (0.1 molar, pH 7.5) was added and the disposable test device was incubated for 2 minutes at room temperature. The membrane was then washed twice with a wash solution (240 µl) containing decyl sulfate (18g/liter) with fluid drained immediately. The leuco dye composition described above was added and the disposable test device was incubated again for 2 minutes at room temperature with fluid drained immediately. The resulting reflectance density on the membranes was determined and converted to transmission density ($D_T$) using standard procedures.

The results of the assays were as follows:

The Invention assay showed only a 4.9% decrease in dye density after the 4 weeks keeping test. Control A showed a 28% loss in dye density while the loss for Controls B and C were 19% and 71%, respectively.

These results indicate that the reagent composition of this invention mixed with poly(acrylamide) had substantially improved keeping stability over those reagents used in admixture with negatively-charged binders. Even the small amount of bovine serum albumin in Control B caused significant stability loss.

EXAMPLES 2-4

Streptococcus A Assay Using Various Binder Materials

The procedure of Example 1 was followed using specific binder compositions containing polymeric particles with lower surface densities of anti-Streptococcus A antibodies. These particles show decreased stability relative to the high density particles used in Example 1, and provide a more sensitive marker for evaluating the stability improvement of the present invention.

The following compositions were evaluated:

Example 1: Specific binding reagent mixed with poly(acrylamide) from the previous example.

Example 2: Specific binding reagent mixed with 5% of poly(N-vinyl-2-pyrrolidone), a neutral binder.

Example 3: Specific binding reagent mixed with 5% of poly[2-(N,N,N-trimethylammonium)ethyl methacarylate chloride-co-2-hydroxyethyl acrylate] (90:10 weight ratio), a positively-charged binder.

Example 4: Specific binding reagent mixed with 5% of poly(dimethyldiallyl ammonium chloride), a positively-charged binder.

Control A: Specific binding reagent mixed with 5% of poly(sulfo-1,1-dimethylethylacrylamide), a negatively-charged binder.

Control B: Specific binding reagent mixed with 5% poly(acrylic acid), a negatively-charged binder.

The results of the assays indicated the following loss of dye density after keeping for 4 weeks at 37° C.:

| | |
|---|---|
| Example 1: | 19% |
| Example 2: | 9% |
| Example 3: | 0% |
| Example 4: | 9% |
| Control A: | 99%* |
| Control B: | 99%* |

*The keeping test was stopped after 2 weeks or less at 37° C.

It can be seen that poly(acrylamide) of Example 1 provided significantly improved stability over the use of the negatively-charged binder in the Controls. However, the binders of Examples 2-4 provided even greater stability.

The invention has been described in detail with particular reference to preferred embodiments thereof, but it will be understood that variations and modifications can be effected within the spirit and scope of the invention.

We claim:

1. A water-insoluble microporous article for use in a ligand-receptor assay to detect a target ligand,
    said article comprising a microporous membrane having first and second opposing outer surfaces, and having coated on at least one of said surfaces a composition comprising a specific binding reagent which comprises water-insoluble particles to which are attached receptor molecules to said target ligand, said reagent admixed with one or more hydrophilic, neutral or positively-charged polymeric binders, wherein substantially none of said reagent is entrapped within said membrane.

2. The article of claim 1 wherein said microporous membrane has an average pore size of from about 0.5 to about 10 μm.

3. The article of claim 1 wherein said receptor molecules are bound to said particles through reactive groups on said particles which are selected from the group consisting of active halo atoms, activated 2-substituted ethylsulfonyl or vinylsulfonyl groups.

4. The article of claim 1 wherein said reagent is affixed to a discrete zone which is less than the total area of said first or second surface.

5. The article of claim 1 wherein said receptor molecules are antibodies to a Streptococcal antigen.

6. The article of claim 5 wherein said receptor molecules are antibodies to a Streptococcus A antigen.

7. The article of claim 1 wherein said polymeric binder is a polymer containing quaternary ammonium salts, a vinylpyrrolidone polymer or an acrylamide polymer.

8. The article of claim 7 wherein said binder is poly(acrylamide), poly[2-(N,N,N-trimethylammonium)ethyl methacrylate chloride-co-2-hydroxyethyl acrylate)], poly(dimethyldiallylammonium chloride) or poly(N-vinyl-2-pyrrolidone).

9. A water-insoluble microporous article for use in an immunoassay to detect Streptococcus A,
    said article comprising a microporous membrane having upper and lower outer surfaces and an average pore size of from about 0.5 to about 10 μm, and having coated on said upper surface a composition comprising an unlabeled specific binding reagent which comprises water-insoluble polymeric particles having an average diameter of from about 0.01 to about 5 μm and to which are attached antibodies to Streptococcus A antigen, said reagent being admixed with one or more hydrophilic polymeric binders which are selected from polymers having quaternary ammonium groups, acrylamide polymers and vinylpyrrolidone polymers, wherein substantially none of said reagent is entrapped within said membrane.

10. The article of claim 9 wherein less than about 1%, by weight, of said reagent is entrapped within said membrane.

11. The article of claim 9 wherein said reagent is coated in a discrete zone which is less than the total area of said upper surface.

12. A method for the detection of a target ligand in a biological specimen comprising the steps of:
    A. contacting a sample of a biological specimen suspected of containing a target ligand with a water-insoluble microporous article,
        said article comprising a microporous membrane having first and second opposing outer surfaces, and having coated on at least one of said surfaces a composition comprising a specific binding reagent which comprises water-insoluble particles to which are attached receptor molecules to said target ligand, said reagent admixed with one or more hydrophilic, neutral or positively-charged polymeric binders, wherein substantially none of said reagent is entrapped within said membrane to form a specific binding complex between said target ligand and said receptor molecules, and
    B. detecting the presence of said complex as an indication of the presence of said ligand in said specimen.

13. The method of claim 12 wherein said specific binding reagent is unlabeled, and prior to, simultaneously with or subsequent to said contact in step A, contacting said target ligand with a detectably labeled receptor molecule so as to form a specific binding complex between said ligand and said labeled receptor in a manner such that ligand complexation with said specific binding reagent is not hindered.

14. The method of claim 12 wherein said specific binding reagent is unlabeled, and prior to, simultaneously with or subsequent to said contact in step A, contacting said specific binding reagent with a predetermined amount of detectably labeled target ligand.

15. A method for the detection of a Streptococcal antigen in a biological specimen comprising the steps of:
    A. contacting a sample of a biological specimen suspected of containing extracted Streptococcal antigen with a water-insoluble microporous article,
        said article comprising a microporous membrane having upper and lower outer surfaces, and having coated on said upper surface a composition comprising an unlabeled specific binding reagent which comprises water-insoluble polymeric particles to which are attached antibodies to said Streptococcal antigen, said reagent admixed with one or more hydrophilic binders selected from polymers containing quaternary ammonium groups, acrylamide polymers and vinylpyrrolidone polymers, wherein substantially none of said reagent is entrapped within said membrane to form a specific binding complex between said Streptococcal antigen and said antibodies, B. prior to, simultaneous with or subsequent to said contact in step A, contacting said Streptococcal antigen with a detectably labeled antibody to said antigen so as to form a labeled specific binding complex of said antigen with both of said labeled reagent and unlabeled antibodies, C. simultaneously with or subsequently to contacting step B, separating said labeled complex from uncomplexed materials by washing uncomplexed materials through said membrane, and D. detecting said labeled complex as an indication of the presence of said Streptococcal antigen in said specimen.

16. The method of claim 15 for the detection of Streptococcus A in said specimen.

17. The method of claim 15 carried out with a disposable test device comprising said water-insoluble microporous article.

18. The method of claim 15 wherein said binder is poly(acrylamide), poly[2-(N,N,N-trimethylammonium)ethyl methacrylate chloride-co-2-hydroxyethyl acrylate)], poly(dimethyldiallylammonium chloride) or poly(N-vinyl-2-pyrrolidone).

19. The method of claim 15 wherein said labeled antibody is a conjugate of antibody and an enzyme, and detection of said labeled complex is accomplished by contacting it with a dye-forming composition for said enzyme.

20. The method of claim 19 wherein said enzyme is peroxidase, and said dye-forming composition comprises hydrogen peroxide and a compound which provides a dye in the presence of both hydrogen peroxide and peroxidase.

21. A diagnostic test kit useful for the detection of a target ligand comprising:

a. a water-insoluble microporous article comprising a microporous membrane having at least first and second opposing outer surfaces, and having coated on at least one of said surfaces a composition comprising an unlabeled specific binding reagent which comprises water-insoluble particles to which are attached receptor molecules to said target ligand, said reagent admixed with one or more hydrophilic, neutral or positively-charged polymeric binders, wherein substantially none of said reagent is entrapped within said membrane and b. detectably labeled receptor molecules.

22. The kit of claim 21 wherein said target ligand is a Streptococcus A antigen, said binder is selected from polymers having quaternary ammonium groups, acrylamide polymers and vinylpyrrolidone polymers, and said unlabeled reagent and labeled receptor molecules are antibodies to said antigen.

23. The kit of claim 21 wherein said binder is poly(acrylamide), poly[2-(N,N,N-trimethylammonium)ethyl methacrylate chloride-co-2-hydroxyethyl acrylate)], poly(dimethyldiallylammonium chloride) or poly(N-vinyl-2-pyrrolidone).

* * * * *